United States Patent
Hering et al.

(10) Patent No.: US 6,598,461 B2
(45) Date of Patent: Jul. 29, 2003

(54) APPARATUS FOR, AND METHOD OF USING, GAS CHROMATOGRAPHY INLET SYSTEM FOR DIRECT ANALYSIS OF SUBSTANCES FIRED FROM AN INKJET PEN

(75) Inventors: Trenton M. Hering, Corvallis, OR (US); Alan L. French, McMinnville, OR (US); Calvin B. Lofton, Lebanon, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 10/000,245

(22) Filed: Oct. 29, 2001

(65) Prior Publication Data

US 2003/0079522 A1 May 1, 2003

(51) Int. Cl.$^7$ .......................... G01N 1/00; G01N 30/04; B41J 29/393; B41J 2/01
(52) U.S. Cl. .................. 73/23.41; 73/23.42; 73/61.55; 73/863.12; 347/19
(58) Field of Search ................ 73/23.35, 23.41, 73/23.25, 23.42, 863.11, 863.12, 864.71, 61.52, 61.55, 61.57; 347/19

(56) References Cited

U.S. PATENT DOCUMENTS

| | | | | |
|---|---|---|---|---|
| 3,847,554 A | * | 11/1974 | Su ............................... 422/80 |
| 4,133,640 A | * | 1/1979 | Clinton et al. ............. 73/23.35 |
| 4,351,802 A | * | 9/1982 | Baylis et al. ................ 422/89 |
| 5,092,926 A | * | 3/1992 | Owatari .................... 106/31.51 |
| 5,588,988 A | * | 12/1996 | Gerstel et al. ............. 73/23.41 |
| 5,596,876 A | * | 1/1997 | Manura et al. ............... 62/55.5 |
| 5,942,699 A | * | 8/1999 | Ornath et al. ............. 73/863.12 |
| 6,223,584 B1 | * | 5/2001 | Mustacich et al. ......... 73/23.41 |
| 6,312,123 B1 | * | 11/2001 | Codos et al. ............... 347/102 |
| 6,395,560 B1 | * | 5/2002 | Markelov .................. 73/23.35 |
| 6,442,995 B1 | * | 9/2002 | van der Maas ............. 73/23.35 |
| 6,488,753 B1 | * | 12/2002 | Ito et al. .................... 106/31.9 |

FOREIGN PATENT DOCUMENTS

| | | | | |
|---|---|---|---|---|
| JP | 362118254 A | * | 5/1987 | ................. 73/23.41 |
| JP | 405052827 A | * | 3/1993 | ............... 73/863.11 |
| JP | 405157742 A | * | 6/1993 | ................. 73/23.35 |

OTHER PUBLICATIONS

Gerstel GmbH & Co. KG; Thermo Desorption System (TDS) catalog; http://www.gerstel.com/en/en_mainframe.html; Aug. 24, 2001.

* cited by examiner

Primary Examiner—Robert R Raevis
Assistant Examiner—Michael Cygan

(57) ABSTRACT

An inlet system is used in conjunction with a standard gas chromatograph/mass spectrometer to facilitate the analysis of volatile components of substances fired from inkjet pens. The system allows for the investigation of changes in the ink resulting from resistor firing. In addition, the system can be used as a diagnostic tool to detect failures in individual firing chamber. After a block is cooled with liquid nitrogen, an analyte sample of ink is deposited on a stage in a chamber in the block and the chamber is then sealed. The stage is then heated vaporizing a portion of the analyte sample. A transfer gas passes over the stage and mixes with vaporized analyte. The mixture then enters a gas chromatography mass spectrometer which determines the analyte sample's components and relative amounts thereof.

41 Claims, 6 Drawing Sheets

APPARATUS FOR, AND METHOD OF USING, GAS CHROMATOGRAPHY INLET SYSTEM FOR DIRECT ANALYSIS OF SUBSTANCES FIRED FROM AN INKJET PEN

BACKGROUND OF THE INVENTION

1. Field of the Invention

This invention relates to the field of testing fired ink from inkjet pens for purposes of analyzing the components of the ink to determine whether an inkjet pen is performing properly.

2. Description of the Related Art

Inkjet pens are widely utilized in printing systems, and are increasingly finding uses in other applications to provide controlled delivery of a wide range of substances. For many reasons, it is advantageous to analyze the actual output from an inkjet pen. However, many quantifiable parameters such as solvent concentrations and thermal degradation products of the ink/printhead interaction are difficult to analyze with traditional gas chromatography injection and mass spectrometry methods due to their volatility and the necessity of producing large quantities of analyte; large analyte quantities are needed due to the inefficiency of traditional sample introduction (i.e., liquid injection).

The current method for analysis of fired ink requires that the pen be fired onto a reasonably clean glass fiber pad; the pad is usually held under the printhead in a Drop Break-off Observation System ("DBOS") (i.e., an optical system having a camera pointed at an inkjet pen which allows an analyst to see the way in which ink drops are formed on a substrate upon being fired by the inkjet pen). Following the firing of the ink onto the glass fiber pad, the current method uses a thermal desorption inlet system coupled to a standard gas chromatograph/mass spectrometer; the gas chromatograph/mass spectrometer analyzes the volatile components of the ink which are released from the glass fiber pads.

After the ink is fired onto the glass fiber pad: (a) the pad is cut to an appropriate size and placed inside a thermal desorption tube which, in turn, is placed within a thermal desorption inlet coupled to a gas chromatograph/mass spectrometer; (b) the inlet to the gas chromatograph/mass spectrometer is closed (i.e., sealed); (c) the carrier gas flow in the gas chromatograph/mass spectrometer is restored; and (d) the inlet zone is heated to an appropriate temperature to achieve thermal desorption. The analyte (i.e., the ink to be analyzed) is mixed with the carrier gas and is swept onto the analytical column where it is cryo-focussed by cooling the gas chromatograph/mass spectrometer oven with a jet of liquid nitrogen. When the analyst determines that the sample has been sufficiently desorbed, the oven temperature is brought to an operating temperature (usually approximately 50° C.) and the analysis begins.

Unfortunately, the traditional analytical method has a plurality of inherent drawbacks which: (a) reduce the integrity of the ink to be analyzed (either by loss of volatile components or by contamination); (b) create an undesirably long analysis duration; (c) require great precision and care when managing the glass pads and depositing the ink thereon; and (d) cause chromatographic peak broadening due to analyte trickling into the column while the analysis is being completed (thereby reducing the benefit cryo-focusing would otherwise generate). These drawbacks are discussed in more detail hereafter.

First, although glass fiber pads are a better substrate than most available materials for thermal desorption, they are not ideal in several respects. For instance, the current method contemplates depositing the ink onto the glass fiber pads at ambient temperatures at which loss of volatile ink components can occur. Moreover, critical amounts of volatile ink components may further be lost when: (a) the glass fiber pads are transferred into the thermal desorption tube associated the gas chromatograph/mass spectrometer; and (b) when the thermal desorption tube is transferred into the gas chromatograph/mass spectrometer. The lost of volatile ink components when the ink is deposited on the glass fiber pads (due to the ambient temperatures at which such transfer occurs) and when the pads are subsequently moved into the desorption tube and then into the gas chromatograph/mass spectrometer can greatly reduce the integrity of the chromatography. In addition, although glass fiber pads are the most suitable substrate for the performance of this traditional method, the pads are known to contribute contaminants to the ink deposited thereon thereby further degrading the integrity of the chromatography.

Glass fiber pads are also problematic for a host of additional reasons. First, by way of example, glass fiber pads must be handled with great care to avoid sample contamination with finger oil, etc. Second, as the analyte ink is only fired onto a portion of the pad, an analyst must choose the area to be analyzed very carefully. Third, the system by which the ink is deposited is particularly inconvenient as the analyst must place the pad precisely, by hand, in the DBOS machine. Fourth, in terms of obtaining accurate analysis results, the analyst must assume that the glass fiber pads (which are not chemically deactivated) do not change the chemical composition of the analyte ink when heated in the inlet liner.

The traditional process itself also suffers from inherent drawbacks. For example, constantly opening and closing the gas chromatograph/mass spectrometer is cumbersome and very time consuming. If one waits until the heated zone in the inlet has cooled to room temperature, each complete analysis can easily take more than an hour and half, thereby severely limiting sample throughput. Unfortunately, it is prudent to cool the inlet in this way to avoid sample oxidation when the inlet liner and sample (and an unavoidable amount of outside air) are introduced into a hot inlet.

Cryo-focusing is traditionally used to avoid introducing the sample into the column over a long period of time, which would broaden analyte chromatographic peaks unacceptably (as the principal advantage of modern capillary column gas chromatography is the superior resolution of sample components in sharp peaks); this advantage is destroyed if the sample mixture is allowed to seep into the instrument over time. By concentrating all of the components of interest in a single, short section of column (which can be easily heated by the gas chromatograph oven), cryo-focusing allows the analyst to start the analysis of the entire sample at once. Unfortunately, in practice, it is possible that the entire sample to be analyzed will not be transferred to the cryogenically cooled analyte column before the analysis is started. As a result, small amounts of less volatile components will continue to trickle into the system during the run and will, thereby, contribute to high background response (i.e., chromatographic peak broadening) and generally poor chromatography. Although this peak broadening is a problem with standard gas chromatographs, it is particularly noticeable in gas chromatograph/mass spectrometers. In addition, such poor chromatography is difficult to avoid using the traditional method as the sample can not be removed from the heated zone until the analysis is complete.

Accordingly, there is a need for an improved method for determining the volatile components of inkjet ink from a complete and functional inkjet pen. In determining the components, the purity and quantity of the sample to be analyzed may be improved by eliminating, or at least reducing one or more of: (a) the amount of contaminants that are added to a sample of inkjet ink to be analyzed; and (b) the amount of volatile ink components lost prior to analysis. In addition, there is a need for an apparatus capable of performing a method having one or more of the aforementioned benefits which is both easy to use and which shortens the duration required for traditional analysis.

SUMMARY OF THE INVENTION

A first embodiment of the invention herein described addresses a gas chromatography inlet system. The inlet system includes a block having a chamber therein accessible through an opening in a side of said block. In addition, the system includes a stage, located in the chamber, which is adapted to receive an analyte sample. The system also contains a temperature adjusting mechanism which is adapted to alter the temperature of the block and stage. A cover is included and is adapted to close the opening in the block. The block has an inlet and an outlet; whereas the inlet is adapted to receive a transfer gas and direct it over the stage, the outlet is adapted to transmit the transfer gas. When the cover closes the opening, the chamber is inaccessible from an exterior of said block except via the inlet and outlet. Further, when the stage is heated by the temperature adjusting mechanism, the apparatus will be capable of vaporizing at least a portion of an analyte sample deposited on the stage.

The temperature adjusting mechanism of this first embodiment of the invention may include a flow of liquid nitrogen. Moreover, if liquid nitrogen is used, it may be used to cool the block and the stage therein before the analyte sample is deposited on the stage. Finally, the stage in the first embodiment may be, and preferably is, glass.

A second embodiment of the invention herein described addresses an analytical apparatus. The analytical apparatus of the second embodiment is similar to the aforementioned first embodiment, however, unlike the previously described first embodiment apparatus, the second embodiment analytical apparatus includes an analytical device. More specifically, the second embodiment apparatus includes a block containing a heating element and having a chamber therein; the chamber is accessible through an opening in a side of said block. A cover is included which is adapted to close the opening in the block. In addition, the apparatus includes a stage, positioned in the chamber, which is adapted to receive an analyte sample. An inlet in the block is adapted to receive a continuous flow of transfer gas and is adapted to direct the continuous flow of the transfer gas over the stage. In addition, an outlet in the block is adapted to receive the transfer gas. The second embodiment also includes an analytical device (as previously mentioned) which is in fluid communication with the outlet. In this second embodiment, when the cover closes the opening, the chamber is inaccessible from an exterior of the block except via the inlet and outlet. In addition, the analytical device is adapted to receive the transfer gas and to determine the components of the analyte sample as supplied thereto in by the transfer gas.

In the second embodiment, the analytical device can be a variety of devices including a gas chromatograph, a mass spectrometer, or a combination gas chromatograph/mass spectrometer. It is also contemplated that the second embodiment may include a temperature adjusting mechanism which is adapted to alter the temperature of the block. If such a temperature adjusting mechanism is included, it could involve a flow of liquid nitrogen.

The second embodiment may also include an intake line, an exhaust line, or both. If the second embodiment includes a temperature adjusting mechanism, it may vaporize an analyte sample deposited on the stage thereby creating an analyte sample vapor which can mix with the transfer gas. Moreover, if an intake line is provided, it can be adapted to transmit a mixture of the transfer gas and the vaporized analyte sample from the block to an inlet in the analytical device. Similarly, if an exhaust line is provided, it can be adapted to transmit a mixture of the transfer gas and the vaporized analyte sample from the block to an exterior of the apparatus.

If the second embodiment includes an intake line and an exhaust line, valves may be positioned in those lines. A first valve may be adapted to prevent the mixture of the transfer gas and the vaporized analyte sample from flowing through the intake line. Moreover, a second valve may be adapted to prevent the mixture of the transfer gas and the vaporized analyte sample from flowing through the exhaust line. It is also conceivable that one connector valve can serve as both the first and the second valves.

The invention described herein also addresses both a method of determining the components in an ink fired from an inkjet pen as well as a method for determining whether an inkjet pen is performing properly. With respect to the method of determining the components in an ink fired from an inkjet pen, the method includes: (a) cooling a block having a stage in a chamber therein; (b) depositing an analyte sample of the ink onto the stage; (c) sealing the chamber; (d) heating the stage to vaporize at least a portion of the analyte sample thereon; (e) passing a transfer gas over the stage so that the vaporized portion of the analyte sample is mixed with the transfer gas forming a gaseous mixture; (f) receiving the gaseous mixture in an analytical device which is in fluid communication with the block; and (g) determining, by means of the analytical device, the components of the gaseous mixture and thereby the components of the vaporized portion of the analyte sample.

In determining the components in an ink fired from an inkjet pen, the analytical device can be any number of devices including a gas chromatograph, a mass spectrometer, or a combination gas chromatograph/mass spectrometer. If a gas chromatograph/mass spectrometer is used as the analytical device, the method may include concentrating the gaseous mixture in the gas chromatograph/mass spectrometer, prior to the step of determining the components of the gaseous mixture (and thereby the components of the vaporized portion of the analyte sample).

In addition, the chamber in the block used in performing the method may have an opening therein. If such an opening is provided, the step of sealing the chamber may include covering the opening with a cover and establishing an airtight closure between the cover and the opening by means of a seal. The step of cooling the block may include passing liquid nitrogen over the block. The method may include, after the steps of cooling of the block and depositing the analyte sample of the ink onto the stage, cyro-focusing the analyte sample on the stage. In addition, the method may also include, prior to the step of cooling the block, heating the stage to remove contaminants thereon.

To ensure that the components of the analyte sample are determined as accurately as possible, it is preferable that the transfer gas be a gas which does not chemically react with the analyte sample; such a non-reactive transfer gas could be helium. Moreover, in determining the components of the analyte sample, the method may include determining the relative amounts of the components in the vaporized portion of the analyte sample.

After a sufficient amount of the gaseous mixture is received in the analytical device, the method of determining the components of the analyte sample may include closing a valve in an intake vessel which carries the gaseous mixture from the chamber to the analytical device; closing the valve in this fashion would prevent additional gaseous mixture from entering the analytical device. If the valve in the intake line is closed, the method may further include opening a valve in an exhaust vessel into which the additional gaseous mixture may flow. Finally, the method may contemplate closing a valve in a transfer gas supply vessel which supplies the transfer gas to the chamber thereby preventing subsequent transfer gas from entering the chamber.

As previously mentioned, the invention also addresses a method for determining whether an inkjet pen is performing properly. This method includes: (a) depositing an analyte sample of ink from an inkjet pen onto a stage in a chamber in a block; (b) heating the stage to vaporize at least a portion of the analyte sample thereon; (c) passing a transfer gas over the stage so that the vaporized portion of the analyte sample is mixed with the transfer gas forming a gaseous mixture; (d) receiving the gaseous mixture in an analytical device which is in fluid communication with the block; (e) determining, by means of the analytical device, the components of the gaseous mixture and thereby the components of the vaporized portion of the analyte sample; and (f) determining, based on the components of the vaporized portion of the analyte sample, whether the inkjet pen is performing properly.

In performing this method for determining whether an inkjet pen is performing properly, the analytical device can be any number of devices including a gas chromatograph, a mass spectrometer, or a combination gas chromatograph/mass spectrometer. In addition, the inkjet pen may comprise a plurality of resistors and/or a plurality of firing chambers. If the inkjet pen comprises a plurality of resistors, the method may include diagnosing improper firing by at least one of the resistors. Similarly, if the inkjet pen comprises a plurality of firing chambers, the method may include diagnosing failures in at least one of the firing chambers.

A structural understanding of the aforementioned gas chromatography/mass spectrometry inlet system and the analytical apparatus, as well as the methods of using the inlet system and the analytical apparatus (to determine inkjet components and whether an inkjet pen is functioning properly), will be easier to appreciate when considering the detailed description in light of the figures hereafter described.

BRIEF DESCRIPTION OF THE DRAWINGS

The accompanying figures, which are incorporated in and constitute a part of the specification, illustrate presently preferred embodiments of the invention. Together with the above general description and the following detailed description, the figures serve to explain the principles of the invention.

DETAILED DESCRIPTION OF THE PREFERRED EMBODIMENT

A solution to one or more of the aforementioned deficiencies in the art can be obtained by a gas chromatography/mass spectrometry inlet system which, in conjunction with a gas chromatograph/mass spectrometer, directly analyzes ink fired from an inkjet pen. In addition, the mechanical solution to the aforementioned deficiencies in the art, which is solved by the apparatus described in detail herein, is used in performing a novel method, also described in detail herein, of analyzing inkjet ink components. Finally, a related method addresses analyzing an ink's components to determine whether an inkjet pen is performing properly.

Figure 1A:
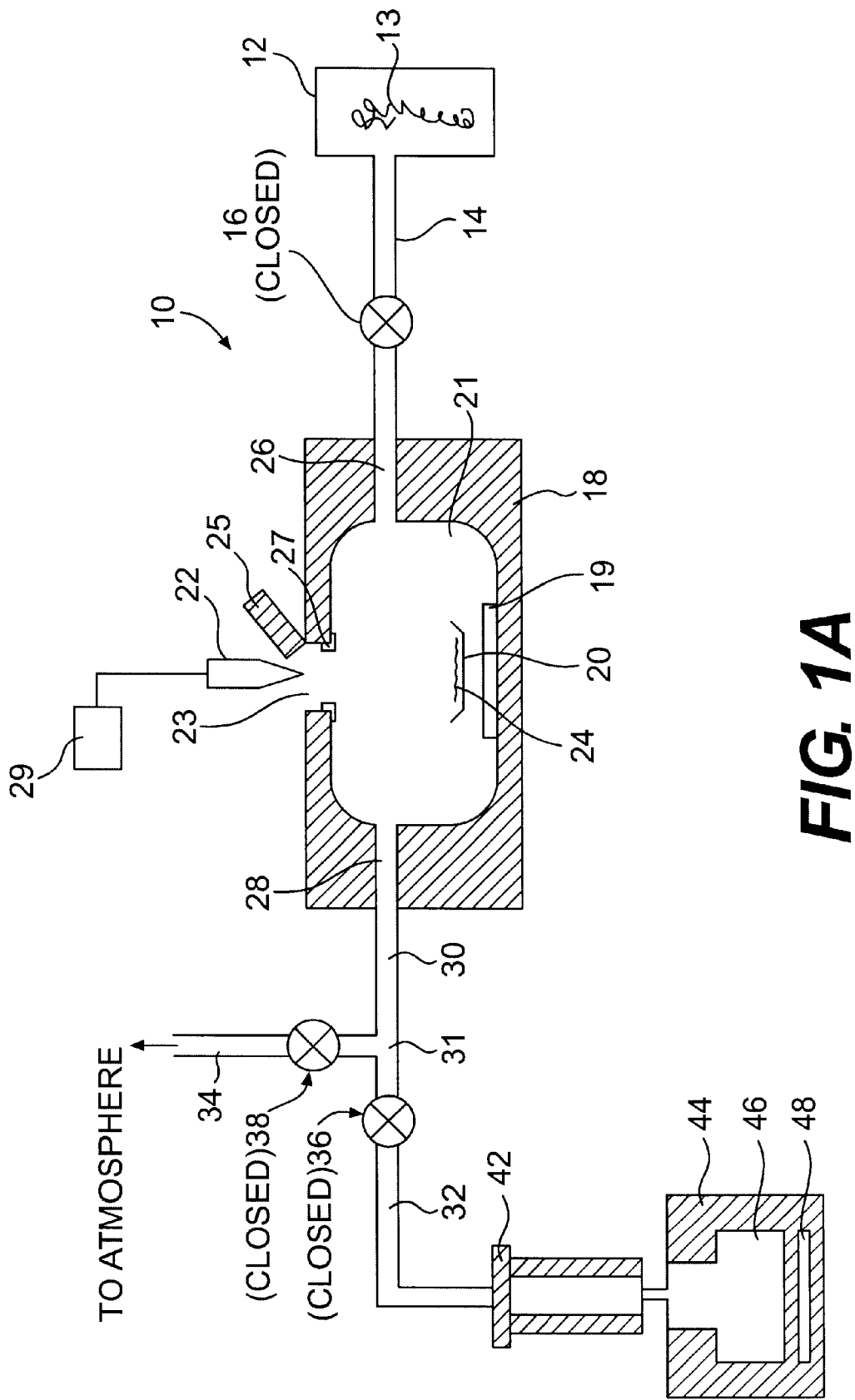
FIG. 1A is a schematic cross-sectional view of an apparatus used in determining the contents of an analyte sample of inkjet ink, the view showing the arrangement of the various apparatus parts prior to depositing the analyte sample on a stage in a chamber in a block.

Referring now to FIG. 1A, there is shown an analytical apparatus 10 in accordance with the present invention. The apparatus 10 described herein has its own heating/cooling components 19, 48 which allow a slowly-responding gas chromatograph inlet 42 to maintain a constant temperature. One novel feature of the apparatus 10 is the way in which the sample is introduced; the apparatus 10 allows a functioning inkjet pen 22 to fire ink directly into a heatable/coolable chamber 21, where the ink, which acts as an analyte sample 24, is captured on a reasonably inert and easily replaceable stage 20.

With respect to a first preferred embodiment, FIGS. 1A, 1B, 2, 3, and 4 show an apparatus 10 used in determining the contents of an analyte sample 24 of inkjet ink. Turning to FIG. 1A, the apparatus 10 includes a block 18 having a chamber 21 formed therein. The chamber 21 is accessible through an opening 23 in a side of the block 18; as is discussed in further detail below, the opening 23 may be closed by a cover 25. The apparatus 10 further includes a stage 20 for receiving an analyte sample 24 to be analyzed. In addition, the apparatus 10 includes a source 12 of transfer gas 13 connected to a transfer gas supply line 14, the supply line 14 leads to a block 18 (the details of which are described, infra). Although the transfer gas 13 can be a variety of gases, it is preferable that it be hydrogen, helium, or nitrogen because they do not readily react with the analyte sample 24. Moreover, among the variety of potential gases, it is most preferable to use helium as it generally performs better than nitrogen and it less explosive than hydrogen.

Figure 1B:
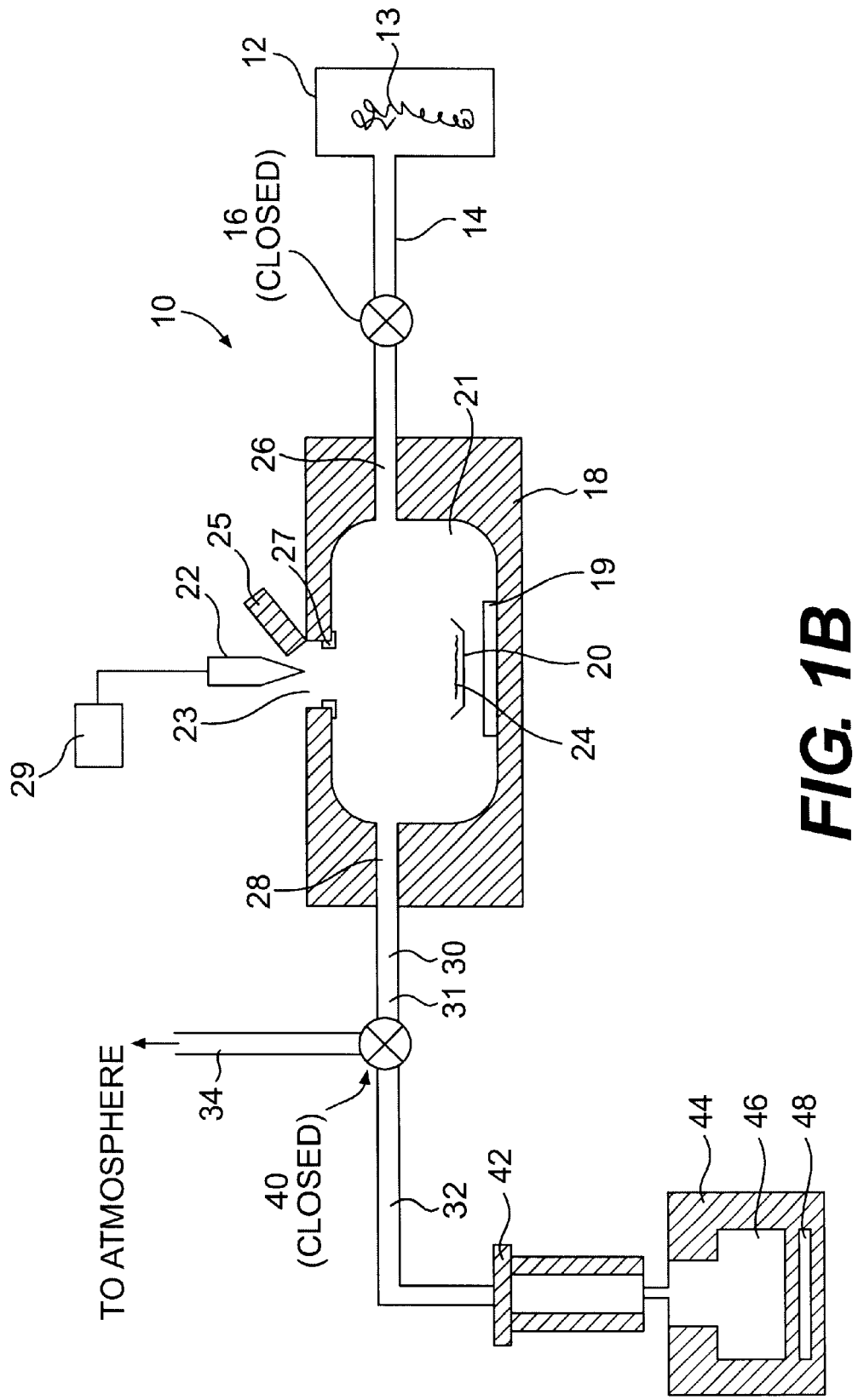
FIG. 1B shows an alternative apparatus which is identical to the apparatus shown in FIG. 1A except for a different valve arrangement.

As shown in FIGS. 1A and 1B, within the transfer gas supply line 14, there is located a transfer gas supply valve 16. Although any valve which functions to prevent the flow of gas can be used for the transfer gas supply valve 16, it is preferable to use a solenoid valve driven by a central controller (not shown). The transfer gas supply line 14, leaving the valve 16, enters the block 18 through an inlet 26. Having passed through the inlet 26, the transfer gas supply line 14 terminates in the chamber 21 in the block 18 with which the transfer gas supply line 14 is in fluid communication.

As previously noted, the chamber 21 in the block 18 has a stage 20 therein. The stage 20 is preferably inert and readily replaceable. Ideally, the stage 20 may be a glass slide. Above the stage 20 there is an opening 23 in the block 18. Although the opening 23 may be closed by any device performing the function of the cover 25, such as, for example, a door hingedly attached to the block 18 (as shown in the figures), it is preferable to use a plug-style hatch due to the improved effectiveness of the airtight engagement between it and the block 18. In addition, the block 18 preferably has a seal 27 around the opening 23 such that when the cover 25 encloses the opening 23, the chamber 21 will be airtight. Above the opening 23, an inkjet pen 22 is positioned by an analyst so that when an analyte sample 24 of inkjet ink is fired by the pen 22, it will be deposited on a predetermined portion of the stage 20. The analyst may position the inkjet pen 22 using a motor 29 which drives the pen 22 in two dimensions parallel to the stage 20 and which may also raise and lower the pen 22 (in a third dimension) with respect to the stage 20.

At a position which is generally opposite the inlet 26, there is formed an outlet 28 in the block 18. The outlet 28, which is in fluid communication with the chamber 18, leads to a transfer line 30 which is adapted to carry the transfer gas 13 and the analyte sample 24 (in vapor form) to an analytical device 44 which is capable of determining the contents of the analyte sample 24. Although the analytical device 44 may be a gas chromatograph, a mass spectrometer, or other device with similar capabilities, it is preferable that it be a combination gas chromatograph/mass spectrometer.

With respect to FIG. 1A, the transfer line 30 contains a "T" connector 31 (or other similar divider, such as a "Y" connector) which divides the transfer line 30 into two separate lines 32, 34. The first line is an intake line 32 which feeds into an inlet 42 of the analytical device 44. The intake line 32 has a valve 36 therein which is preferably a solenoid valve. The second line is an exhaust line 34, the function of which will become clearer, infra. Similar to the intake line 32, the exhaust line 34 has a valve 38 therein which is also preferably a solenoid valve.

It is possible, as shown in FIG. 1B, to include one connector valve 40 in a central portion of the connector 31 rather than the two valves 36, 38 in the intake line 32 and the exhaust line 34, respectively. The connector valve 40 would have at least three possible configurations: (a) a closed completely configuration in which no gas flows through the valve 40 to either the intake line 32 or to the exhaust line 34; (b) an intake open/exhaust closed configuration in which gas flows from the transfer line 30 to the intake line 32 but not to the exhaust line 34; and (c) an intake closed/exhaust open configuration in which gas flows from the transfer line 30 to the exhaust line 34 but not to the intake line 32.

Figure 2:
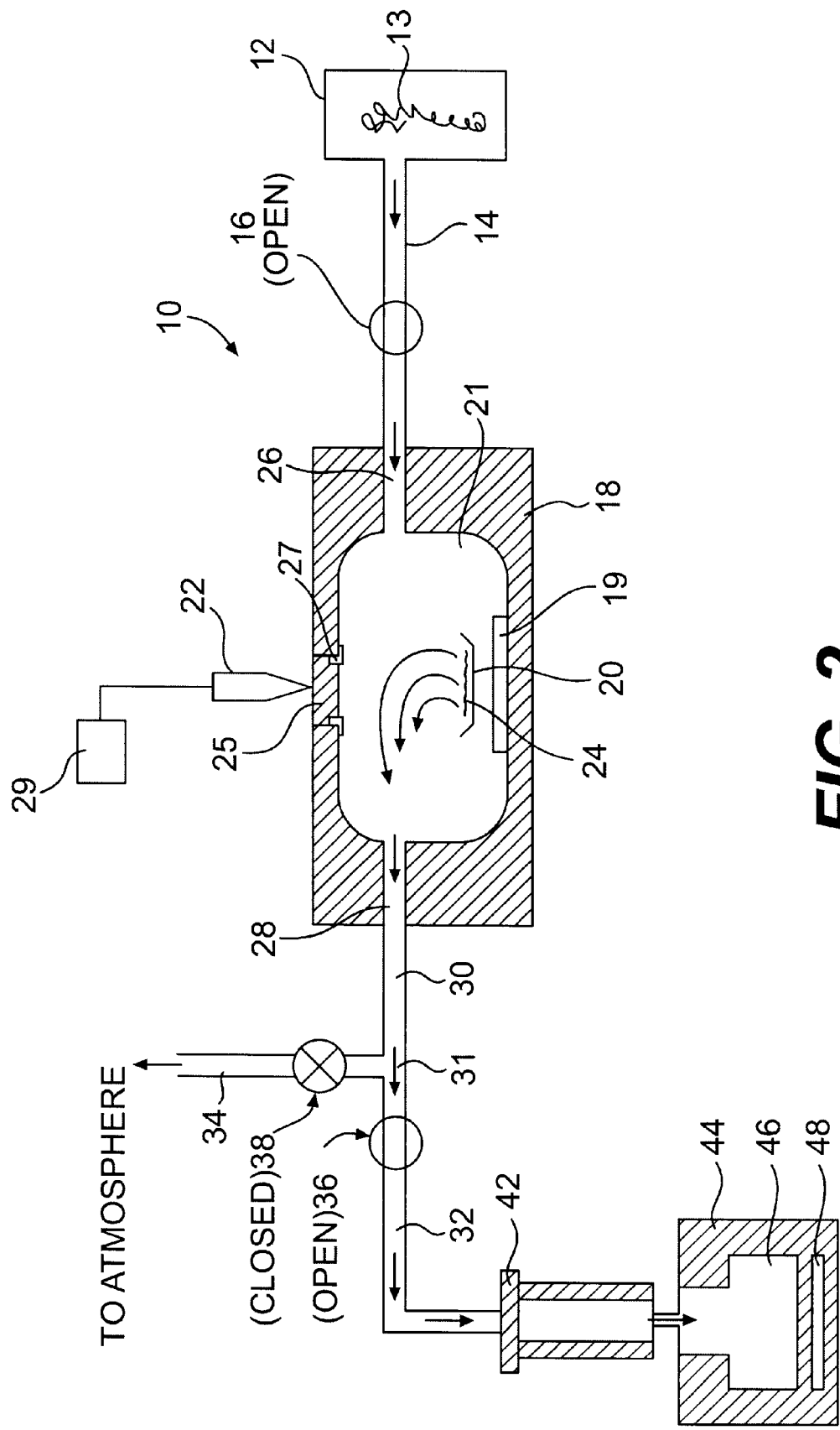
FIG. 2 is a schematic cross-sectional view of the apparatus in FIG. 1A showing the door of the block closed and the chamber exposed to a transfer gas which carries the heated analyte to an analytical device capable of determining the contents of the analyte.
Figure 3:
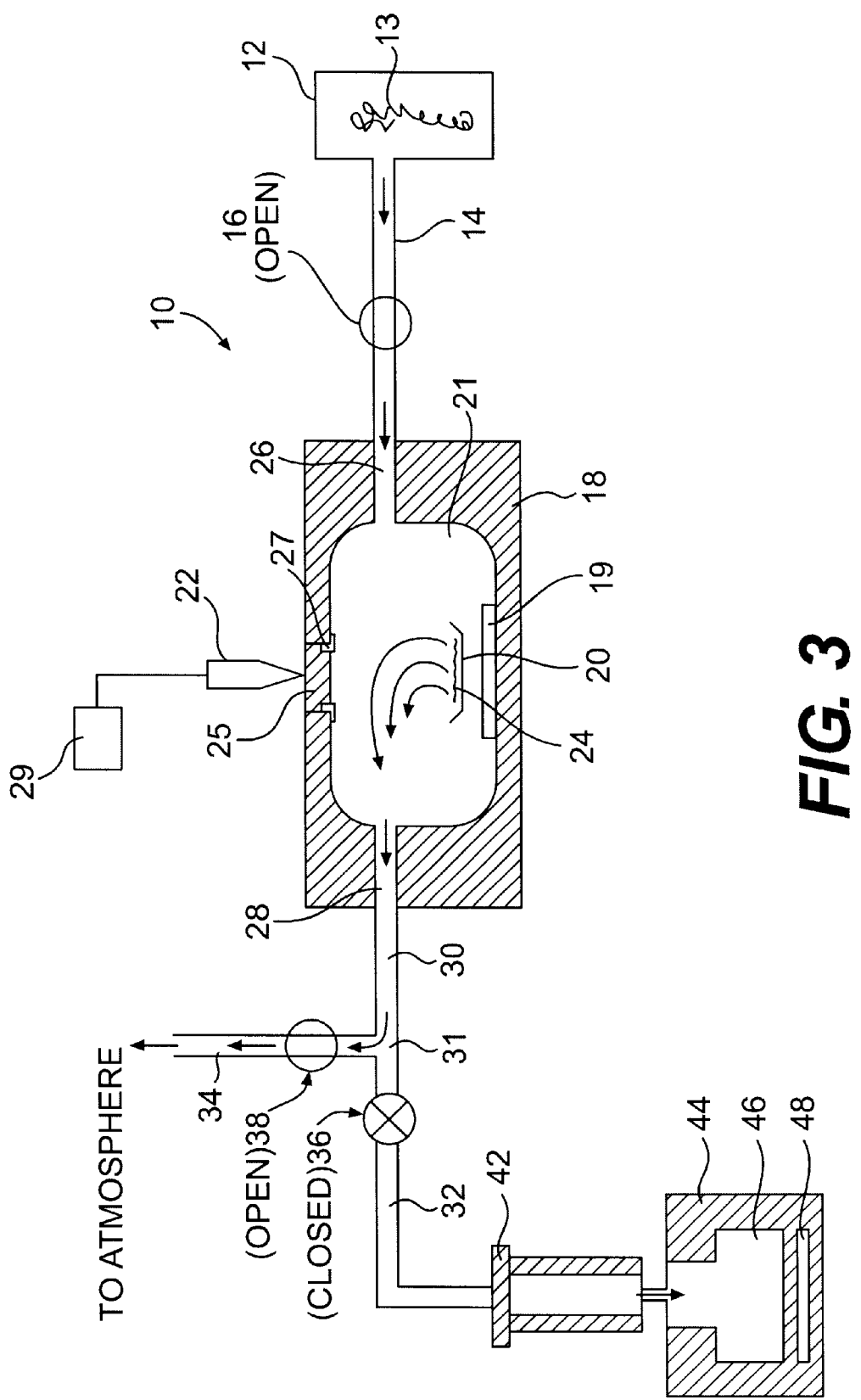
FIG. 3 is a schematic cross-sectional view of the apparatus in FIG. 1A showing a valve in an intake line being closed and a second valve in an exhaust line being open while the analytical device determines the contents of the analyte sample.

Although one valve 40 may be used in the connector 31 (as previously described), as shown in FIGS. 2 and 3, it is also possible to use the two separate valves 36, 38 shown in FIG. 1A to accomplish the same function. FIG. 2 shows that when the valve 36 in the intake line 32 is open and when the valve 38 in the exhaust line 34 is closed, the same overall gas flow is achieved as when the valve 40 in the connector 31 is set to the configuration in which gas can flow to the intake line 32 but not to the exhaust line 34. Similarly, FIG. 3 shows that where the valve 36 in the intake line 32 is closed and where the valve 38 in the exhaust line 34 is open, the same overall gas flow is achieved as when the valve 40 in the connector 31 is set to the configuration in which gas can flow to the exhaust line 34 but not to the intake line 32.

Adjusting the configuration of the connector valve 40 (in FIG. 1B), or opening or closing the valves 36, 38 in the intake line 32 and in the exhaust line 34 (in FIG. 1A), respectively, could be determined by a controller (not shown). Moreover, the controller may be similar to (or the same as) the controller which controls the valve 16 in the transfer gas supply line 14.

Regardless of valve design chosen to allow for the transfer gas 13 to: (a) remain in the transfer line 30; (b) flow through the intake line 32; or (c) flow through the exhaust line 34, the apparatus 10 contemplates that at certain times transfer gas 13, containing analyte sample 24 vapor, will be transmitted through the intake line 32 and into the analytical device 44. If a gas chromatograph (or a combination gas chromatograph/mass spectrometer) is chosen for the analytical device 44, the transfer gas 13 and analyte sample vapor will pass through the intake line 32 and into a gas chromatograph inlet 42 which is in fluid communication therewith. The temperature of the inlet 42 is regulated, as later described in more detail. Having passed through the inlet 42, the transfer gas 13 and analyte sample 24 vapor will enter the gas chromatograph 44, and, more particularly, into a gas chromatography column 46 in the gas chromatograph 44. The chromatography column 46 is heated by a gas chromatograph oven 48 positioned within the gas chromatograph 44. As later described in more detail, an analytical run of the gas chromatograph 44 will occur when a sufficient amount of the analyte sample 24 is received within the chromatography column 46.

The operation of the apparatus 10 will now be described. Initially, the cover 25 to the chamber 21 in the block 18 is removed/opened thereby exposing the chamber 21 to the atmosphere and, more importantly, to the inkjet pen 22. At this time, the block 18 may be preferably cryogenically cooled with liquid nitrogen administered by a temperature adjusting mechanism 19. By way of contrast, the intake line 32 is heated to a temperature above the maximum anticipated temperature which will be experienced by the chamber 21 to prevent condensation of vaporized analyte sample 24 vapor passing through intake line 32 (as described below). In addition, the valve 16 in the transfer gas supply line 14 is closed thereby preventing any transfer gas 13 from entering the chamber 21. Moreover, if the apparatus of FIG. 1A is used, the valves 36, 38 in the intake line 32, and in the exhaust line 34, respectively, are closed. Similarly, if the apparatus in FIG. 1B is used, the valve 40 in the connector 31 in the transfer line 30 is set to the configuration in which no transfer gas 13 passes into the intake line 32 or into the exhaust line 34.

If an older gas chromatograph/mass spectrometer inlet 42 is used (i.e., one which does not thermally desorb the analyte sample 24), the gas chromatograph inlet 42, like the intake line 32, is hot thereby preventing the analyte sample 24 vapor from condensing therein. By way of contrast, if a modern gas chromatograph/mass spectrometer inlet 42 is used (i.e., one which thermally desorbs the analyte sample), the inlet is cryogenically cooled. Regardless of the inlet 42 used, the gas chromatograph oven 48 is cryogenically cooled. Although either type of inlet 42 can be used, it is preferable to use a thermally desorbing inlet, such as a Gerstel CIS3 inlet.

Figure 4:
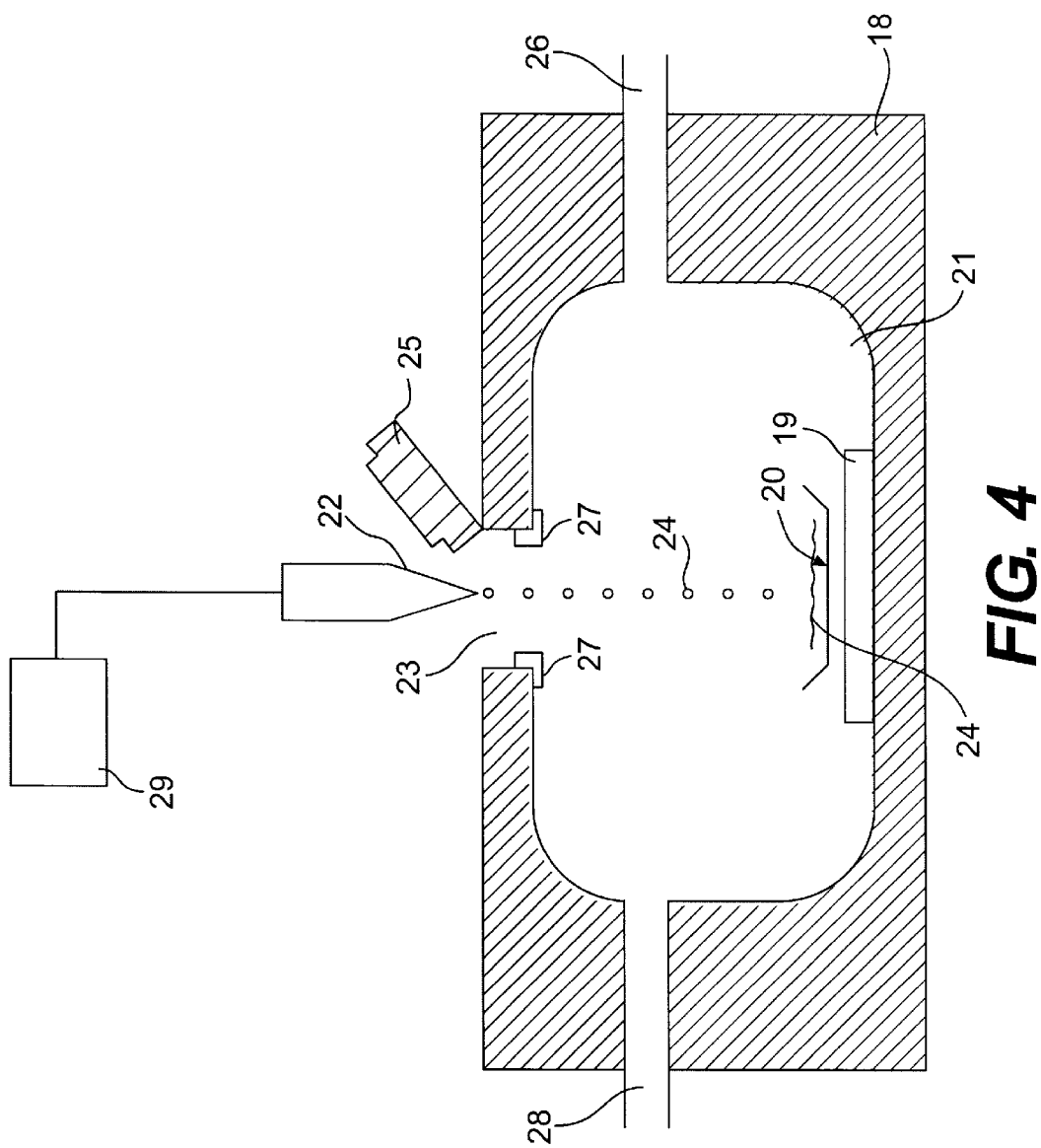
FIG. 4 is a cross-sectional view of the block of the apparatus shown in FIGS. 1A and 1B showing the stage, the analyte sample, and the inkjet pen.

As shown in FIG. 4, an inkjet pen 22 is then carefully positioned, by a motor 29, to deposit an analyte sample 24 onto a predetermined portion of the stage 20; the stage should be as free from contaminants as is reasonably possible. When the inkjet pen 22 is properly positioned, the analyte sample 24 is fired from the pen 22 onto the predetermined portion of the stage 20. If the block 18 was cryogenically cooled, as preferred, the analyte sample is cryo-focussed on the stage 20. Turning to FIG. 2, after the analyte sample 24 is fired onto the stage 20, the cover 25 (i.e., door) to the chamber 21 is closed and engages the airtight seal 27 thereby sealing the chamber 21 from the atmosphere.

When the chamber 21 has been properly sealed, the valve 16 in the transfer gas supply line 14 is opened allowing the transfer gas 13 (supplied by the transfer gas source 12) to enter the chamber 21. In addition, if the apparatus of FIG. 1A is chosen, the valve 36 in the intake line 32 is opened whereas the valve 38 in the exhaust line 34 remains closed. Similarly, if the apparatus in FIG. 1B is used, the valve 40 in the connector 31 is switched to the configuration in which gas can flow into the intake line 32 but not into the exhaust line 34.

After the chamber 21 has been swept with several volumes of inlet transfer gas, the surrounding block 18 is slowly heated by the temperature adjusting mechanism 19. At this time, as the heat is applied to the block 18, the stage 20 located within the chamber 21 is heated by the heating mechanism 19. As the block 18 is heated, at least a portion of the analyte sample 24 on the stage 20 is vaporized; the volatile components of the analyte sample 24 (which are in gaseous form) are then swept-up by the transfer gas 13 passing through the chamber 21. The transfer gas 13 carries the analyte sample 24 vapor to the inlet 42 of the analytical device 44 by way of the transfer line 30 and the intake line 32. The analytical device 44 functions in a traditional fashion (i.e., there is a split or splitless transfer of the analyte sample vapor 24 onto the chromatography column 46).

We turn now to FIG. 3 while considering the apparatus of FIG. 1A. Provided that the analytical device 44 is a gas chromatograph/mass spectrometer and provided that it has its own supply of chromatographic carrier gas (which is used in performing the chromatography therein), when a sufficient amount of analyte sample 24 is received in the chromatography column 46 in the analytical device 44 (as easily determined by one of ordinary skill in the art), the analyst will close the valve 36 in the intake line 32 and open the valve 38 in the exhaust line 34. Similarly, if the FIG. 1B apparatus is used, the analyst will switch the valve 40 in the connector 31 to prevent flow through the intake line 32 but to allow flow through the exhaust line 34.

Figure 1C:
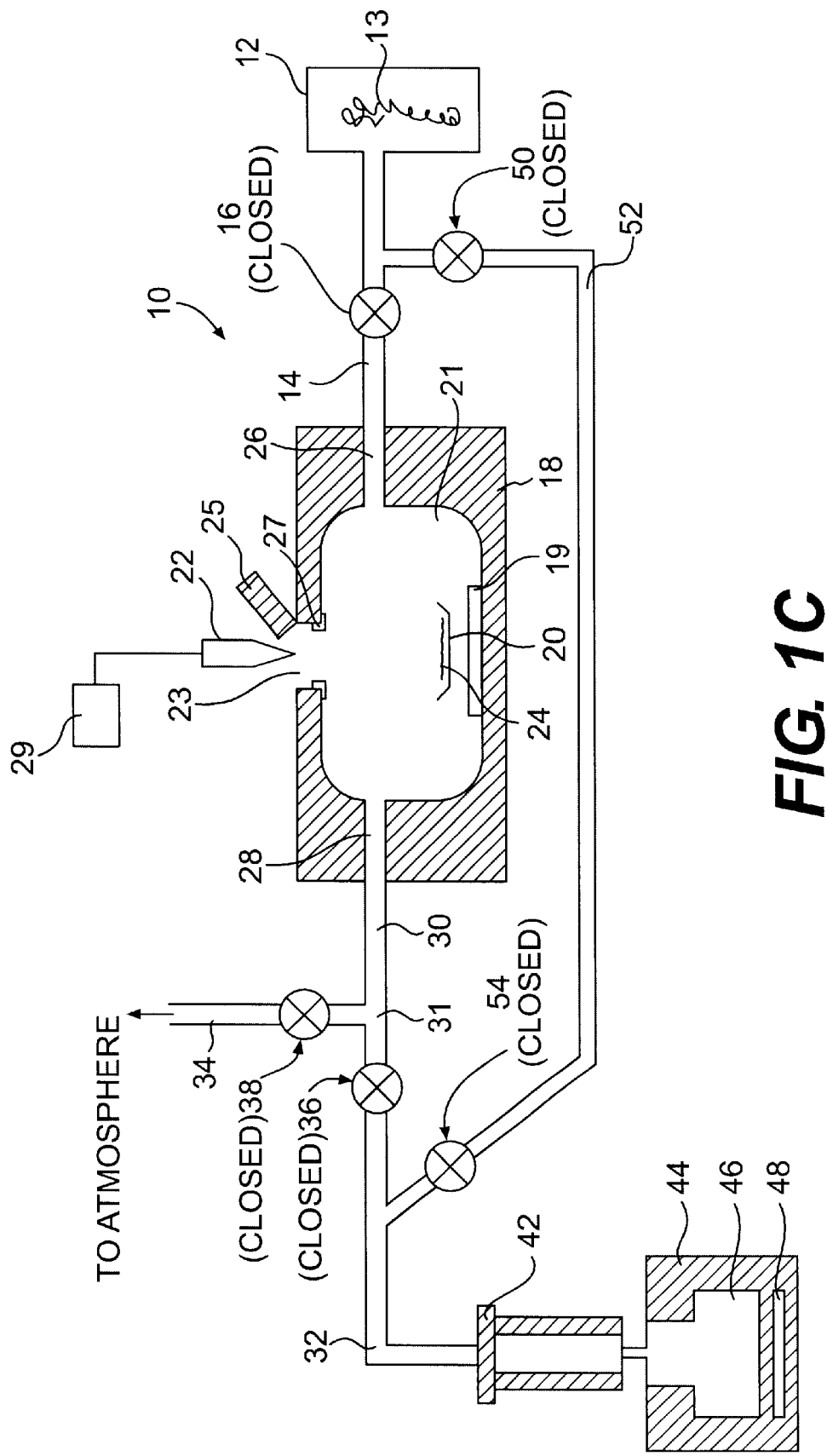
FIG. 1C shows an alternative to the apparatus shown in FIG. 1A having a bypass line which could also be incorporated into the apparatus shown in FIG. 1B.

It should be noted (as shown in FIG. 1C), however, that if the analytical device 44 does not have its own supply of carrier gas, one could place another valve 50 in the vicinity of the transfer gas supply line 14 and connect thereto a bypass line 52 which would extend to another valve 54 in the vicinity of the intake line 32. Until a sufficient amount of analyte sample 24 is accumulated in the chromatograph column 46, access to and from the bypass line 52 will be precluded (i.e., the valves 50, 54 would be closed). However, once a sufficient amount of analyte is accumulated in the column 46, access to the bypass line 52 would begin (i.e., the valves 50, 54 would be opened while the valve 36 would be closed, as previously described) thereby allowing the transfer gas 13 to serve as the carrier gas necessary for chromatograph process to occur.

Although FIG. 1C shows the apparatus of FIG. 1A having the additional bypass line 52, it is to be readily understood that a similar alteration could be made to the apparatus 10 shown in FIG. 1B. Moreover, one could replace the valve 16 in the transfer gas supply line 14 with a connector valve (similar to the connector valve 40). However, it should also be appreciated that is it preferred to use an analytical device 44 having its own supply of carrier gas so that the overall design of the system can be correspondingly simpler.

Regardless of the way in which the carrier gas is supplied, once a sufficient amount of analyte sample 24 vapor is received in the chromatograph column 46, the analytical process will commence. Meanwhile, the block 18 will continue to be heated causing the residual analyte sample 24 on the stage 20 to be baked-off and carried out of the chamber 21 by the transfer gas 13; the baked-off analyte sample 24 leaves the apparatus 10 by means of the exhaust line 34.

When no analytical sample 24 remains on the stage 20, the user will close the valve 16 in the transfer gas supply line 14 and will close the valve 38 in the exhaust line 34 (if the apparatus in FIG. 1A is used) or will switch the valve 40 in the connector 31 to prevent flow to either the intake line 32 or the exhaust line 34 (if the apparatus in FIG. 1B is used). In addition, the cover 25 will be removed thereby exposing the chamber 21 to the atmosphere. Moreover, the heating of the block 18 will be terminated. To reduce the overall cycle time, the block 18 may then be preferably cryogenically cooled by the temperature adjusting mechanism 19 to the temperature it experienced when the analyte sample 24 was originally deposited thereon. While the block 18 is being cooled, the analysis performed by the analytical device 44 continues until completed. At this time, if necessary the stage 20 may be replaced. After the block 18 and the stage 20 are sufficiently cooled, the apparatus 10 is ready for the next sampling cycle (provided that the analysis being performed by the analytical device 44 is finished).

The analytical process determines the contents and percentages of the volatile compounds in the analyte sample 24. For example, if the analytical process is standard gas chromatography, the result would be a two-dimensional plot showing peaks corresponding to each of the volatile components of the analyte sample 24; a standard plot would be of elution time versus intensity. The area under the peaks, as determined by integration (which is a common function of modern gas chromatographs) would correspond directly to the percentage of each component of the analyte sample 24.

Similarly, if the analytical process is mass spectrometry, the result would be a two dimensional plot of mass/charge versus intensity. The plot would show spikes at the mass/charge locations corresponding to each component in the analyte sample 24; the height of the spikes (i.e., the intensity) would correspond to the percentage of each component in the analyte sample 24. As anyone of ordinary skill in the art would appreciate, both of the aforementioned percentages may be readily attained using a standard gas chromatograph/mass spectrometer.

The results of the analytical process can be used to determine whether an inkjet pen 22 is performing properly. Specifically, after the components (and their relative percentages) of the analyte sample 24 are determined, the analyst can compare the results with control results taken from inkjet pens known to be functioning properly. In this manner, the analyst can determine, based on differences from the actual results and the control results whether, for example, there is a problem resulting from improper resistor firing in the inkjet pen 22. In addition, the system can be used as a diagnostic tool to detect failures in individual firing chambers.

The exemplary embodiments described above may be used to analyze any substance fired from an inkjet pen, and are not limited to inks. Thus the invention is applicable to all of the wide range of applications to which inkjet technology is increasingly being applied.

Although the aforementioned described various embodiments of the invention, the invention is not so restricted. The foregoing description is for exemplary purposes only and is not intended to be limiting. Accordingly, alternatives which would be obvious to one of ordinary skill in the art upon reading the teachings herein disclosed, are hereby within the scope of this invention. The invention is limited only as defined in the following claims and equivalents thereof.

We claim:

1. A gas chromatography inlet system, comprising:
   a block having a chamber therein accessible through an opening in a side of said block;
   a stage in the chamber provided below the opening, said stage being adapted to receive an analyte sample falling under gravity through the opening;
   a temperature adjusting mechanism which is adapted to alter the temperature of the block and stage therein;
   a cover adapted to close the opening in said block;
   an inlet in said block adapted to receive a transfer gas, said inlet being adapted to direct the transfer gas over said stage; and
   an outlet in said block adapted to transmit the transfer gas,
   wherein when said cover closes the opening, the chamber is inaccessible from an exterior of said block except via the inlet and outlet, and wherein when said stage is heated by the temperature adjusting mechanism, the apparatus will be capable of vaporizing at least a portion of an analyte sample deposited on the stage.

2. The gas chromatography inlet system according to claim 1, wherein the temperature adjusting mechanism includes a flow of liquid nitrogen.

3. The gas chromatography inlet system according to claim 2, wherein the liquid nitrogen is adapted to cool the block and the stage therein before the analyte sample is deposited on the stage.

4. The gas chromatography inlet system according to claim 1, wherein the stage is glass.

5. The gas chromatograph inlet system according to claim 1, wherein the analyte sample is inkjet ink.

6. The gas chromatography inlet system according to claim 1, wherein the analyte sample is deposited on the stage by a dispenser.

7. The gas chromatography inlet system according to claim 6, wherein the dispenser is an inkjet pen.

8. The gas chromatography inlet system according to claim 1, further comprising:
   an inlet valve positioned between the inlet and a source of the transfer gas; and
   an outlet valve in fluid communication with the outlet.

9. The gas chromatography inlet system according to claim 8, further comprising:
   means for opening and closing the inlet and outlet valves.

10. The gas chromatograph inlet system according to claim 1, wherein the analyte sample is deposited on a predetermined portion of the stage.

11. An analytical apparatus comprising:
    a block containing a heating element and having a chamber therein accessible through an opening in a side of said block;
    a cover adapted to close the opening in said block;
    a stage in the chamber provided below the opening, said stage being adapted to receive an analyte sample falling under gravity through the opening;
    an inlet in said block adapted to receive a continuous flow of transfer gas and adapted to direct the continuous flow of the transfer gas over said stage;
    an outlet in said block adapted to receive the transfer gas; and
    an analytical device in fluid communication with the outlet, said analytical device being adapted to receive the transfer gas,
    wherein when said cover closes the opening, the chamber is inaccessible from an exterior of said block except via the inlet and outlet, and wherein the analytical device is adapted to determine the components of the analyte sample.

12. The analytical apparatus according to claim 11, further comprising:
    a temperature adjusting mechanism which is adapted to alter the temperature of the block.

13. The analytical apparatus according to claim 12, wherein the temperature adjusting mechanism includes a flow of liquid nitrogen.

14. The analytical apparatus according to claim 12, further comprising:
    an intake line,
    wherein the temperature adjusting mechanism is adapted to vaporize an analyte sample deposited on the stage, and wherein the intake line is adapted to transmit a mixture of the transfer gas and the vaporized analyte sample from the block to an inlet in the analytical device.

15. The analytical apparatus according to claim 14, further comprising:
    an exhaust line,
    wherein the exhaust line is adapted to transmit a mixture of the transfer gas and the vaporized analyte sample from the block to an exterior of the apparatus.

16. The analytical apparatus according to claim 14, further comprising:
    a first valve,
    wherein the first valve is adapted to prevent the mixture of the transfer gas and the vaporized analyte sample from flowing through the intake line.

17. The analytical apparatus according to claim 16, further comprising:
    a second valve,
    wherein the second valve is adapted to prevent the mixture of the transfer gas and the vaporized analyte sample from flowing through the exhaust line.

18. The analytical apparatus according to claim 17, wherein the first and the second valves are the same valve.

19. The analytical apparatus according to claim 11, wherein the analytical device is a gas chromatograph, a mass spectrometer, or a combination gas chromatograph/mass spectrometer.

20. The analytical apparatus according to claim 11, wherein the analyte sample is inkjet ink.

21. The analytical apparatus according to claim 11, wherein the analyte sample is deposited on the stage by a dispenser.

22. The analytical apparatus according to claim 21, wherein the dispenser is an inkjet pen.

23. The analytical apparatus according to claim 11, wherein the analyte sample is deposited on a predetermined portion of the stage.

24. The analytical apparatus according to claim 11, further comprising:
    an inlet valve positioned between the inlet and a source of the transfer gas; and
    an outlet valve in fluid communication with the outlet.

25. The analytical apparatus according to claim 24, further comprising:

means for opening and closing the inlet and outlet valves.

26. A method of determining the components in an ink fired from an inkjet pen comprising the steps of:
cooling a block having a stage in a chamber therein;
depositing an analyte sample of the ink onto the stage;
sealing the chamber;
heating the stage to vaporize at least a portion of the analyte sample thereon;
passing a transfer gas over the stage so that the vaporized portion of the analyte sample is mixed with the transfer gas forming a gaseous mixture;
receiving the gaseous mixture in an analytical device which is in fluid communication with the block;
determining, by means of the analytical device, the components of the gaseous mixture and thereby the components of the vaporized portion of the analyte sample;
closing a valve in an intake vessel which carries the gaseous mixture from the chamber to the analytical device, after a sufficient amount of the gaseous mixture is received in the analytical device, thereby preventing additional gaseous mixture from entering the analytical device; and
opening a valve in an exhaust vessel into which the additional gaseous mixture flows.

27. The method according to claim 26, wherein the analytical device is a gas chromatograph, a mass spectrometer, or a combination gas chromatograph/mass spectrometer.

28. The method according to claims 26, wherein the chamber in the block has an opening, said step of sealing the chamber comprises the steps of:
covering the opening with a cover; and
establishing an airtight closure between the cover and the opening by means of a seal.

29. The method according to claim 26, wherein the analytical device is a gas chromatograph/mass spectrometer, said method further comprising the step of:
concentrating the gaseous mixture in the gas chromatograph/mass spectrometer, prior to the step of determining the components of the gaseous mixture and thereby the components of the vaporized portion of the analyte sample.

30. The method according to claim 26, wherein the step of cooling the block comprises:
passing liquid nitrogen over the block.

31. The method according to claim 26, further comprising the step of:
heating the stage to remove contaminants thereon, prior to the step of cooling the block.

32. The method according to claim 30, further comprising the step of:
heating the stage to remove contaminants thereon, prior to the step of cooling the block.

33. The method according to claim 26, wherein the transfer gas does not chemically react with the analyte sample.

34. The method according to claim 33, wherein the transfer gas is helium.

35. The method according to claim 26, wherein the step of determining, by means of the analytical device, the components of the gaseous mixture and thereby the components of the vaporized portion of the analyte sample comprises:
determining the relative amounts of the components in the vaporized portion of the analyte sample.

36. The method according to claim 26, further comprising the steps of:
closing a valve in a transfer gas supply vessel which supplies the transfer gas to the chamber to thereby prevent subsequent transfer gas from entering the chamber.

37. The method according to claim 30, further comprising:
cyro-focusing the analyte sample on the stage, after the steps of cooling of the block and depositing the analyte sample of the ink onto the stage.

38. A method for determining whether an inkjet pen is performing properly, said method comprising the steps of:
depositing an analyte sample of ink from the inkjet pen onto a stage in a chamber in a block;
heating the stage to vaporize at least a portion of the analyte sample thereon;
passing a transfer gas over the stage so that the vaporized portion of the analyte sample is mixed with the transfer gas forming a gaseous mixture;
receiving the gaseous mixture in an analytical device which is in fluid communication with the block;
determining, by means of the analytical device, the components of the gaseous mixture and thereby the components of the vaporized portion of the analyte sample; and
determining, based on the components of the vaporized portion of the analyte sample, whether the inkjet pen is performing properly,
wherein said inkjet pen comprises a plurality of resistors, and wherein the step of determining, based on the components of the vaporized portion of the analyte sample, whether the inkjet pen is performing properly comprises:
diagnosing improper firing by at least one of said plurality of resistors.

39. The method according to claim 38, wherein the analytical device is a gas chromatograph, a mass spectrometer, or a combination gas chromatograph/mass spectrometer.

40. A method for determining whether an inkjet pen is performing properly, said method comprising the steps of:
depositing an analyte sample of ink from the inkjet pen onto a stage in a chamber in a block;
heating the stage to vaporize at least a portion of the analyte sample thereon;
passing a transfer gas over the stage so that the vaporized portion of the analyte sample is mixed with the transfer gas forming a gaseous mixture;
receiving the gaseous mixture in an analytical device which is in fluid communication with the block;
determining, by means of the analytical device, the components of the gaseous mixture and thereby the components of the vaporized portion of the analyte sample; and
determining, based on the components of the vaporized portion of the analyte sample, whether the inkjet pen is performing properly,
wherein said inkjet pen comprises a plurality of firing chambers, and wherein the step of determining, based on the components of the vaporized portion of the analyte sample, whether the inkjet pen is performing properly comprises:
diagnosing failures in at least one of said plurality of firing chambers.

41. The method according to claim 40, wherein the analytical device is a gas chromatograph, a mass spectrometer, or a combination gas chromatograph/mass spectrometer.

* * * * *